US011282298B2

(12) United States Patent
Mehl et al.

(10) Patent No.: US 11,282,298 B2
(45) Date of Patent: Mar. 22, 2022

(54) MONITORING THE PERFORMANCE OF PHYSICAL EXERCISES

(71) Applicant: Kaia Health Software GmbH, Munich (DE)

(72) Inventors: Konstantin Mehl, Munich (DE); Maximilian Strobel, Munich (DE)

(73) Assignee: KAIA HEALTH SOFTWARE GMBH, New York, NY (US)

( * ) Notice: Subject to any disclaimer, the term of this patent is extended or adjusted under 35 U.S.C. 154(b) by 0 days.

(21) Appl. No.: 16/113,507

(22) Filed: Aug. 27, 2018

(65) Prior Publication Data
US 2019/0362139 A1 Nov. 28, 2019

(30) Foreign Application Priority Data

May 28, 2018 (EP) .................................... 18174657

(51) Int. Cl.
*G06T 7/73* (2017.01)
*G06T 7/246* (2017.01)
(Continued)

(52) U.S. Cl.
CPC ............ *G06V 40/23* (2022.01); *A61B 5/1116* (2013.01); *A61B 5/1118* (2013.01);
(Continued)

(58) Field of Classification Search
None
See application file for complete search history.

(56) References Cited

U.S. PATENT DOCUMENTS

| 9,154,739 B1 | 10/2015 | Nicolaou et al. |
| 2012/0190505 A1 | 7/2012 | Shavit et al. |

(Continued)

FOREIGN PATENT DOCUMENTS

| CN | 105787439 A | 7/2016 |
| CN | 107103613 A | 8/2017 |

(Continued)

OTHER PUBLICATIONS

Rougier et al. "Procrustes Shape Analysis for Fall Detection," Author manuscrip, published in The English International Workshop on Visual Survelliance, inna-00325643, version 1, Sep. 29, 2008, XP55521763, 8 pages.

(Continued)

*Primary Examiner* — Idowu O Osifade
(74) *Attorney, Agent, or Firm* — Birch, Stewart, Kolasch & Birch, LLP

(57) ABSTRACT

A method for monitoring a person performing a physical exercise based on a sequence of image frames showing the person's exercise activity is described. The method comprises the steps of extracting, based on the sequence of image frames, for each image frame a set of body key points using a neural network, the set of body key points being indicative of the person's posture in the image frame, and deriving, based on a subset of the body key points in each image frame, at least one characteristic parameter indicating the progression of the person's movement. The method further comprises detecting a start loop condition by evaluating the time progression of at least one of the characteristic parameters, said start loop condition indicating a transition from a start posture of the person to the person's movement when performing the physical exercise.

18 Claims, 6 Drawing Sheets

(51) Int. Cl.
*A61B 5/11* (2006.01)
*A61B 5/00* (2006.01)
*G06V 40/20* (2022.01)
*A63B 24/00* (2006.01)

(52) U.S. Cl.
CPC ............ *A61B 5/1128* (2013.01); *A61B 5/725* (2013.01); *A61B 5/7405* (2013.01); *A63B 24/0062* (2013.01); *G06T 7/248* (2017.01); *G06T 7/74* (2017.01); *A63B 2024/0068* (2013.01); *A63B 2220/806* (2013.01); *A63B 2230/62* (2013.01); *G06T 2207/10016* (2013.01); *G06T 2207/20084* (2013.01); *G06T 2207/30196* (2013.01)

(56) References Cited

U.S. PATENT DOCUMENTS

| | | | |
|---|---|---|---|
| 2013/0226039 | A1 | 8/2013 | Shani et al. |
| 2014/0270387 | A1 | 9/2014 | Hoof et al. |
| 2015/0005910 | A1* | 1/2015 | Ishii ............... G06K 9/00342 700/91 |
| 2015/0325004 | A1 | 11/2015 | Utsunomiya et al. |
| 2017/0087416 | A1 | 3/2017 | Hu et al. |
| 2017/0177930 | A1 | 6/2017 | Holohan |
| 2017/0316578 | A1* | 11/2017 | Fua ..................... G06T 7/246 |
| 2018/0018779 | A1 | 1/2018 | Lu et al. |
| 2018/0285697 | A1* | 10/2018 | Shotton ............ G06K 9/6219 |
| 2019/0362506 | A1* | 11/2019 | Leroyer ............... G06T 7/97 |
| 2020/0237266 | A1* | 7/2020 | Qiao ................. G06K 9/481 |

FOREIGN PATENT DOCUMENTS

| | | |
|---|---|---|
| EP | 2 612 221 B1 | 1/2018 |
| JP | 2016-80671 A | 5/2016 |
| WO | WO 2014/151700 A1 | 9/2014 |
| WO | WO 2015/164421 A1 | 10/2015 |

OTHER PUBLICATIONS

López et al., "Movement Analysis in Learning by Repetitive Recall. An Approach for Automatic Assistance in Physiotherapy", Departamento de Engenharia Elétrica Universidade Federal do Espirito Santo-UFES, 2012, 8 pages, XP-32189694A.
Hossain et al., "Exploiting temporal information for 3D pose estimation", CoRR, 2017, 17 pages.
Howard et al., "MobileNets: Efficient Convolutional Neural Networks for Mobile Vision Applications", arXiv:1704.04861v1, 2017, 9 pages.
Martinez et al., "A simple yet effective baseline for 3d human pose estimation", IEEE International Conference on Computer Vision, vol. 206, May 2017, 10 pages.
Newell et al., "Stacked Hourglass Networks for Human Pose Estimation", European Conference on Computer Vision, Springer International Publishing, Oct. 2016, 17 pages.
Zhou et al., "Towards 3D Human Pose Estimation in the Wild: a Weakly-supervised Approach", IEEE International Conference on Computer Vision, Oct. 2017, 10 pages.
A. H. Kargar B. et al., "Automatic Measurement of Physical Mobility in Get-Up-and-Go Test Using Kinect Sensor", Aug. 26, 2014, pp. 3492-3495.
D. Mehta et al., "VNect: Real-time 3D Human Pose Estimation with a Single RGB Camera", ACM Transactions on Graphics, vol. 36, No. 4, Article 44, Publication date Jul. 2017, pp. 44:1-44:14.
F. Ahmed et al., "Kinect-Based Gait Recognition Using Sequences of the Most Relevant Joint Relative Angles", Journal of WSCG, No. 2, vol. 23, 2015, pp. 147-156.
F. Bogo et al., "Keep it SMPL: Automatic Estimation of 3D Human Pose and Shape from a Single image", Springer international Publishing AG 2016, Sep. 2016, Part V, Lncs 9909, pp. 561-578.
F. Muijzer, "Master Thesis, Development of an Automated Exercise Detection and Evaluation System Using the Kinect Depth Camera", Jan. 29, 2014, pp. 1-113.
H. M. Hondor et al., "A Review on Technical and Clinical impact of Microsoft Kinect on Physical Therapy and Rehabilitation", Hindawl Publishing Corporation Journal of Medical Engineering, Jun. 2014, Article ID 846514, 16 pages.
J. C. Nunez et al., "Convolutional Neural Networks and Long Short-Term Memory for skeleton-based human activity and hand gesture recognition". Pattern Recognition 76 (Apr. 2018) pp. 80-94.
J. Cancela et al., "Proposal of a Kinect(tm)-based system for gait assessment and rehabilitation in Parkinson's disease". Annu Int Conf IEEE Eng Med Biol Soc. 2014;2014:4519-22. doi: 10.1109/EMBC.2014.6944628, pp. 4519-4522.
L. Pishchulin et al., DeepCut Joint Subset Partition and Labeling for Multi Person Pose Estimation, Nov. 2015, IEEE Conference on Computer Vision and Pattern Recognition (CVPR), pp. 4929-4937.
M. Ye et al., "Gait Phase Classification for In-Home Gait Assessment", 978-1-5090-6067-2/Jul. 17, 2017 IEEE.
S. Jiang et al., "Real Time Gait Recognition System based on Kinect Skeleton Feature", pp. 1-12, Apr. 2015.
S. Laraba et al., "3D skeleton-based action recognition by representing motion capture sequences as 2D-RGB images", Wiley, Mar. 2017, pp. 1-11.
T. B. Moeslund et al., (eds.), "Visual Analysis of Humans", DOI 10.1007/978-0-85729-997-08, Springer-Verag London Limited 2011, 10 pages.
W. Cho et al., "Human Action Classification Using Procrustes Shape Theory", Proc. of SPIE-IS&T, vol. 9405, pp. 94050T-1-94050T-7, 2015.
W. Z. W. Z. Abiddin et al., "Development of Matlab Kinect Skeletal Tracking System (MKSTS) for Gait Analysis", 978-1-5090-1543-6/May 16, 2016 IEEE, pp. 216-220.
W. Zhao et al., "Rule-Based Human Motion Tracking for Rehabilitation Exercises: Realtime Assessment, Feedback, and Guidance", IEEE Access, Special Section on Intelligent Systems for the internet of Things, vol. 5, 2017, p. 21382-21394.
X. Perez-Sala et al., Subspace Procrustes Analysis, Int J Comput Vis (2017) 121, pp. 327-343.

* cited by examiner

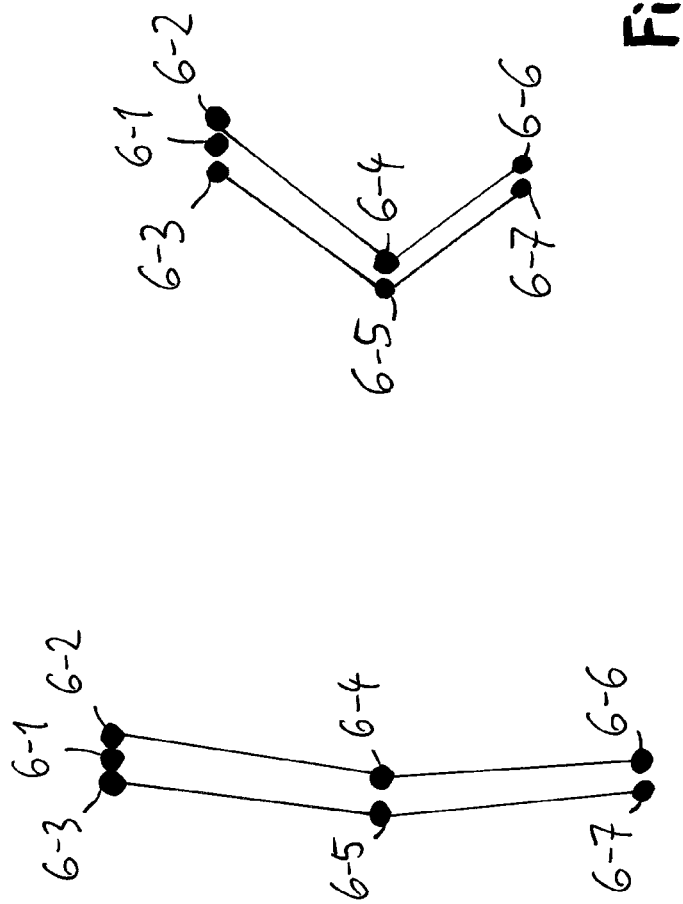

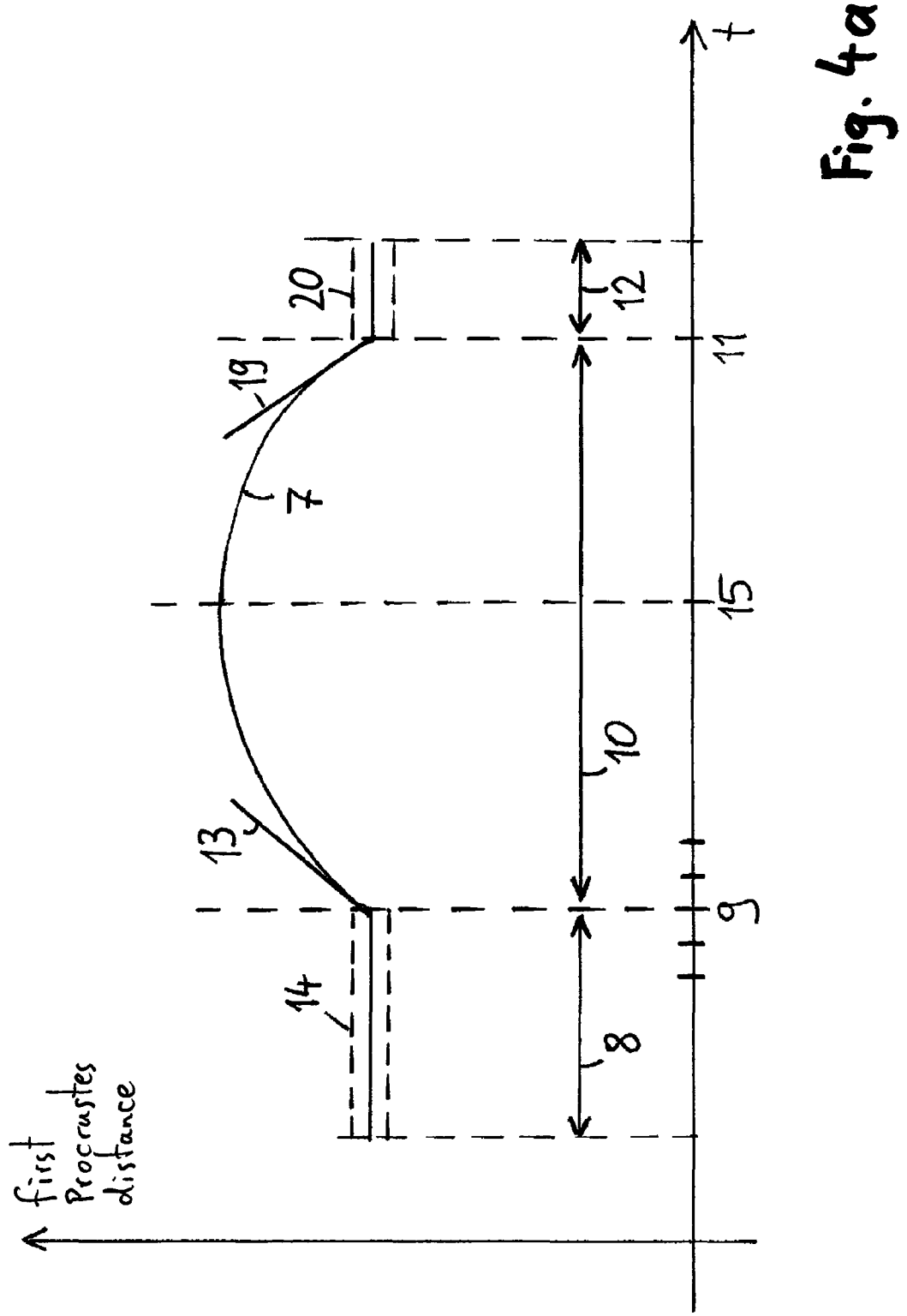

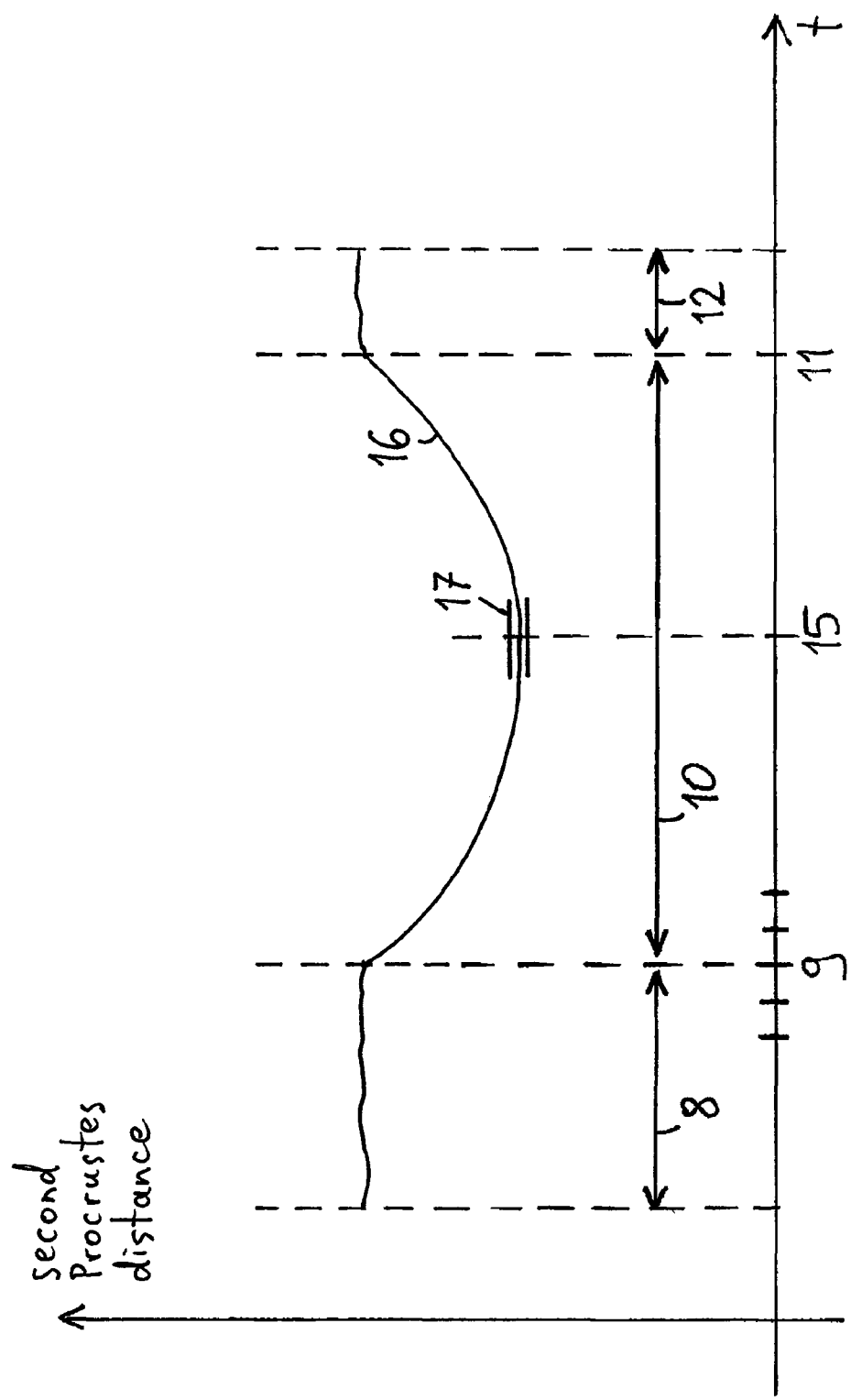

MONITORING THE PERFORMANCE OF PHYSICAL EXERCISES

FIELD OF THE INVENTION

The invention relates to a method for monitoring a person performing a physical exercise based on a sequence of image frames showing the person's exercising activity. The invention further relates to a mobile device with an evaluation unit configured for performing the method and to a computer program product.

BACKGROUND OF THE INVENTION

Physical exercise provides an important contribution for improving a person's state of health. For example, in the field of physiotherapy, major improvements of a patient's state of health can be achieved if a patient performs regular exercising.

US patent application US 2013/0226039 A1 describes a method for analysing and monitoring mobility abnormalities of human patients. The method includes the following stages: capturing a physiotherapeutic sequence of a scene that includes 3D positioning and orientations of the body parts of the human patient over time; monitoring, over a physiotherapeutic session, the set of key points on the human patient while the human patient performs physiotherapeutic exercises comprising a set of predefined sequences of body-related and limb-related postures and gestures; and analysing the monitored set of key points during the physiotherapeutic session, to yield an assessment of a level of compliance of the human patient in performing the physical training or physiotherapeutic exercises, based at least partially on the abnormality mobility profile. Additionally, an analysis during the physiotherapeutic session may be carried out, to yield an assessment of a level of compliance of the human patient in performing specified physiotherapeutic exercises.

OBJECT OF THE INVENTION

The object of the invention is to provide a method for monitoring a person performing physical exercising and to evaluate the person's exercising activity.

SUMMARY OF THE INVENTION

According to the invention, a method for monitoring a person performing a physical exercise based on a sequence of image frames showing the person's exercise activity is provided. The method comprises steps of extracting, based on the sequence of image frames, for each image frame a set of body key points using a neural network, the set of body key points being indicative of the person's posture in the image frame and deriving, based on a subset of the body key points in each image frame, at least one characteristic parameter indicating the progression of the person's movement. The method further comprises detecting a start loop condition by evaluating the time progression of at least one of the characteristic parameters, said start loop condition indicating a transition from a start posture of the person to the person's movement when performing the physical exercise.

Different persons perform physical exercises at different speeds, and accordingly, it is challenging to evaluate the person's movement. According to the present invention, a set of body key points is derived for each image frame of the sequence of image frames using a neural network. A body key point is a point at a predetermined position of the person's body, for example at a joint, a limb or any other body feature of the person's body. Analysis by means of a neural network is well suited for identifying the respective positions of joints, limbs and other body features of the human body. The body key points indicate the person's posture in each of the image frames. For tracking the progression of the person's movement during one or more repetitions of the physical exercise, at least one characteristic parameter is used, said at least one characteristic parameter being derived based on a subset of the body key points. Hence, analysis of the sequence of image frames can be performed at two different levels. For example, the person's posture can be evaluated using the set of body key points and in addition to that, the overall movement of the person during physical exercising can be monitored using the at least one characteristic parameter. In particular, by evaluating the time progression of at least one of the characteristic parameters, it is possible to detect when a start loop condition is fulfilled. The start loop condition is configured for indicating a transition from the start posture to the person's exercising activity. In order to detect when the start loop condition is fulfilled, the at least one characteristic parameter is analysed as a function of time. The start posture is the posture from which the respective physical exercise is started. The start posture may for example be a static posture or it may for example comprise a start motion, for example a regular start motion from which the respective physical exercise is started. The start loop condition allows determining the point of time when the person starts performing the respective exercise. Detecting the correct start point of physical exercising is essential for evaluating the person's movement. Even if the speed of performing the exercise and the way the exercise is performed is completely different for different persons, it is still possible to determine the underlying time frame of the person's movement. This allows evaluating the person's movement both in space and in time.

Further according to the invention, a method for monitoring a person performing a physical exercise based on a sequence of image frames showing the person's exercise activity is provided. The method comprises steps of extracting, based on the sequence of image frames, for each image frame a set of body key points using a neural network, the set of body key points being indicative of the person's posture in the image frame, and deriving, based on a subset of the body key points in each image frame, at least one characteristic parameter indicating the progression of the person's movement. The method further comprises steps of detecting at least one evaluation point in the person's movement by evaluating the time progression of at least one of the characteristic parameters and evaluating the person's posture in a respective image frame at each evaluation point or in at least one image frame in a respective predefined time interval around each evaluation point.

For monitoring the person performing a physical exercise, a set of body key points is extracted for each image frame of the sequence of image frames. A body key point is a point at a predetermined position of the person's body, for example at a joint, a limb or any other body feature of the person's body. The body key points indicate the person's posture in each of the image frames. In addition to the body key points, at least one characteristic parameter is extracted from a subset of the body key points, with said at least one characteristic parameter describing the person's movement when performing the physical exercise. By evaluating the time progression of at least one of the characteristic parameters, at least one evaluation point can be detected. For detecting the at least one evaluation point, the course of at least one of the characteristic parameters is analysed as a function of time. An evaluation point is a point in time at which the person's posture is evaluated. For example, at the evaluation point, the person's posture can be analysed in more detail. Instead of analysing the person's complete movement, only the postures at the at least one evaluation point are evaluated. Thus, the computational burden is reduced. By correctly identifying meaningful evaluation points in the course of performing the exercise, significant postures can be identified and evaluated. Priority is given to the identification and evaluation of the relevant postures at the at least one evaluation point, with these relevant postures being analysed. As a result, the quality of the evaluation is improved. For example, based on this evaluation, a qualified feedback may be given to the person.

Further according to the invention, a mobile device is provided. The mobile device comprises a processor, a memory, a camera and an evaluation unit, the camera being configured for acquiring a sequence of image frames. The evaluation unit comprises a neural network configured for extracting, for each image frame of the sequence of image frames showing a person performing an exercise, a set of body key points indicative of the person's posture. The evaluation unit is configured for performing the above described methods for monitoring the person performing a physical exercise.

Further according to the invention, a computer system comprising a mobile device and a cloud server is provided. The mobile device comprises a processor, a memory, a camera and an interface. The camera is configured for acquiring a sequence of image frames. The interface of the mobile device is configured for transmitting the image data to a cloud server. At the cloud server, a neural network is provided, the neural network being configured for extracting, for each image frame of the sequence of image frames showing a person performing an exercise, a set of body key points indicative of the person's posture. The cloud server is configured for performing the above described methods for monitoring the person performing a physical exercise. Preferably, feedback is transmitted from the evaluation unit to the mobile device.

Further according to the invention, a computer system comprising a camera, a transmitter connected to the camera and a remote computer or cloud server is provided. The camera is configured for acquiring a sequence of image frames and the transmitter is configured for transmitting the image data to a remote computer or a cloud server. At the remote computer or at the cloud server, a neural network is provided, the neural network being configured for extracting, for each image frame of the sequence of image frames showing a person performing an exercise, a set of body key points indicative of the person's posture. The remote computer or the cloud server is configured for performing the above described methods for monitoring the person performing a physical exercise.

Yet further according to the invention, a computer program product is provided, the computer program product being adapted to cause, when executed by a mobile device or a computer comprising a processor and a memory, the mobile device or the computer to perform the above described methods for monitoring a person performing a physical exercise.

Preferred Embodiments of the Invention

Preferred features of the invention which may be applied alone or in combination are discussed below and in the dependent claims.

Preferably, the start loop condition is configured for detecting the transition from a start posture to physical exercising. Further preferably, the start loop condition indicates the start of one or more loops of physical exercising, with a loop encompassing one single repetition of the physical exercise. The person may perform one loop of physical exercising, but in general, a sequence of several loops or repetitions of a physical exercise is performed.

Tracking Propagation of a Characteristic Parameter

Preferably, the method comprises evaluating a propagation of at least one of the characteristic parameters in the course of time. The at least one characteristic parameter is analysed as a function of time. The at least one characteristic parameter is chosen such that the person's motion when performing the exercise can be tracked. For example, by tracking at least one of the characteristic parameters, the start and the end of the person's physical activity can be monitored.

In a preferred embodiment, at least one of the characteristic parameters for a certain image frame is a parameter derived from coordinate values of a subset of body key points in the respective frame. For example, coordinate values of several body key points may be combined or averaged in order to yield a characteristic parameter that is indicative of the person's motion. In this regard, for different physical exercises, a different subset of body key points may for example be selected. Further preferably, at least one of the characteristic parameters for a certain image frame is a parameter derived from coordinate values of the body key points in the respective frame, wherein probabilities associated with the body key points are considered, said probabilities being obtained as an output of the neural network.

Preferably, at least one of the characteristic parameters for a certain image frame is a coordinate value of a specific body key point in the respective frame. In this very simple solution, a coordinate value of one single body key point is used for tracking the person's motion. For example, when a person performs squats, the vertical position of the hip may be taken as a characteristic parameter for tracking the motion. According to an alternatively preferred embodiment, the at least one characteristic parameters is not equal to any coordinate value of a body key point. In this embodiment, the at least one characteristic parameter differs from the body key points' coordinate values.

Preferably, for each of the image frames, at least one of the characteristic parameters is the Procrustes distance between the subset of body key points in a respective frame and the same subset of body key points in a reference frame. The Procrustes distance between two subsets of body key points provides a measure for the difference in shape between the two subsets. For performing a Procrustes analysis, the two subsets are brought into alignment by scaling, rotating, translating and reflecting one subset relative to the other. The Procrustes distance may for example be obtained as the sum of the squared differences of the points in the first and the second subset of body key points. Accordingly, the Procrustes distance indicates the change in shape. For this reason, the Procrustes distance is well suited for tracking the person's motion when performing an exercise.

Preferably, the reference frame is a predefined reference frame showing the subset of body key points. The reference frame may for example be an image frame showing a posture of the person that performs the exercise or an image frame showing a posture of a different person. Alternatively, the reference frame may solely depict a configuration of body key points. The reference frame may for example be a predefined external reference frame showing at least a subset of the body key points. As the Procrustes analysis comprises steps of scaling, rotating, translating and reflecting, the respective subset of body key points in the reference frame can be brought into alignment with the body key points showing the person performing the exercise even if the body key points of the reference frame relate to a different person with different proportions, body size etc.

Preferably, for each of the image frames, at least one of the characteristic parameters is the Procrustes distance between the subset of body key points in a respective frame and the same subset of body key points in an image frame showing the person's start posture. Preferably, the method comprises a step of determining, for each image frame, a Procrustes distance between the subset of body key points in the respective frame and the subset of body key points in an image frame showing the person's start posture.

Preferably, for each of the image frames, at least one of the characteristic parameters is the Procrustes distance between the subset of body key points in a respective frame and the same subset of body key points in an image frame at an evaluation point in the person's movement. Further preferably, the image frame at the evaluation point shows a significant posture of the person. Preferably, the method comprises a step of determining, for each image frame, a Procrustes distance between the subset of body key points in the respective frame and the subset of body key points in an image frame at the evaluation point.

Preferably, the body key points extracted for each image frame are 2D points. Preferably, the sequence of image frames is acquired using a 2D camera. In an alternatively preferred embodiment, the body key points extracted for each image frame are 3D points, wherein the sequence of image frames is acquired using a 2D camera or a 2.5D camera. The additional depth information of the body key points can be derived from 2D or 2.5D image frames acquired using a 2D or 2.5D camera, because using the techniques of machine learning, it is possible to derive additional depth information from a 2D image frame or from a sequence of 2D image frames. Mainly because of body constraints, machine learning allows for estimating additional depth information from 2D image frames. In an alternatively preferred embodiment, the body key points extracted for each image frame are 2.5D points or 3D points, wherein the sequence of image frames is acquired using a 2.5D camera or a 3D camera. In this case, the 2.5D camera or 3D camera provides the additional depth information. Preferably, the Procrustes distance is determined in 2D for a subset of 2D body key points. According to an alternatively preferred embodiment, the Procrustes distance is determined in 2.5D or 3D for a subset of 2.5D or 3D body key points. Procrustes analysis can be performed in two dimensions, but it can also be performed in three dimensions.

Preferably, at least one of the characteristic parameters is obtained as a result of a filtering operation applied to a subset of the body key points in the sequence of image frames. Preferably, at least one of the characteristic parameters is obtained by subjecting a subset of the body key points to Kalman filtering. The Kalman filter is an efficient recursive filter that estimates the internal state of a linear dynamic system for a series of noisy measurements. Preferably, by subjecting a subset of body key points to Kalman filtering, estimates of at least one of velocity and acceleration of at least one of the body key points are obtained as characteristic parameters indicating the progression of the person's movement. For example, a linear velocity or an angular velocity of a respective body key point or an angle enclosed by specific body key points may be obtained as a result of Kalman filtering. In particular, different variants of Kalman filters, such as for example extended Kalman filters, can be used.

Preferably, at least one of the characteristic parameters is derived from a subset of body key points in the sequence of image frames using machine learning. Machine learning may for example be applied to the body key points in a way that at least one characteristic parameter is derived that is suitable for detecting a transition from the start posture to exercising activity. As a further example, at least one characteristic parameter may be derived that is suitable for detecting at least one evaluation point in the course of the person's movement.

Further preferably, the method comprises a step of automatically selecting the subset of body key points in dependence on the respective physical exercise. For different exercises, different subsets of body key points may be suited for tracking the person's movement. For example, when performing squats, the hip, the knees and the ankles may be of relevance.

Preferably, the method comprises a step of detecting a setup position in which the person stands in front of the camera facing the camera. It is advantageous to use this position as a setup position, because it allows determining the proportions of the person's body, which may be used in the course of further evaluation. Preferably, the person's setup position is evaluated based on at least a subset of the body key points. Preferably, in case the person has not assumed the setup position yet, feedback is provided to the person. Thus, the person may be guided to the setup position. Preferably, for evaluating the setup position and providing suitable feedback, a set of feedback trigger conditions is used. Further preferably, the method comprises a step of detecting a first setup position in which the person stands in front of the camera facing the camera and a second setup position in which the person stands sideways to the camera. Further preferably, the body key points extracted for at least one of the front view and the side view of the person are used for calibrating the image frames of the sequence of image frames.

According to a specific embodiment, detecting a setup position in which the person stands in front of the camera facing the camera comprises evaluating a ratio between the shoulder distance and the distance from thorax to pelvis. Thus, it is possible to determine if the person is standing upright in front of the camera facing the camera.

Detecting a Start Posture

Preferably, the method comprises a step of detecting a start posture of the person by comparing the person's posture in at least one image frame of the sequence of image frames with at least one predefined criterion. The start posture is the posture from which the respective physical exercise is started. If the predefined criterion is fulfilled, the person is in the start posture. For example, the start posture may be identified by evaluating the respective positions of at least a subset of the body key points. Preferably, the start posture is a rest position of the person.

Preferably, detecting the start posture comprises analysing at least one of distances, angles, proportions, ratios of the set of body key points in an image frame. By evaluating these geometric properties, it can be determined that the person is in the start posture.

Detecting a Start Loop Condition

In a preferred embodiment, the start loop condition is a condition indicating the start of the person's exercising activity. The start loop condition is configured such that a transition from the person's start posture to exercising activity can be detected. Accordingly, the exercising activity starts in the image frame in which the start loop condition is fulfilled. By applying the start loop condition to the course of at least one of the characteristic parameters, the image frame in which exercising starts can be detected.

Preferably, the start loop condition is configured for detecting when a transition from the person's start posture to the person's exercising activity occurs. By detecting the start loop condition, ie by detecting when the start loop condition is fulfilled, the transition from the start posture to the person's exercising activity can be detected. Preferably, this transition can be detected by evaluating the time progression of at least one of the characteristic parameters. Preferably, the transition can be detected by applying the start loop condition to the time progression of at least one of the characteristic parameters. The course of at least one of the characteristic parameters is analysed as a function of time.

Preferably, for detecting the start loop condition, at least one of the following is evaluated as a function of time: the time course of at least one of the characteristic parameters, a first derivative with respect to time of at least one of the characteristic parameters and a second derivative with respect to time of at least one of the characteristic parameters. Optionally, higher order derivatives may be considered as well.

Further preferably, a time progression of at least one of the characteristic parameters is compared with a predefined template indicating a typical time behaviour of at least one of the characteristic parameters that corresponds to the start loop condition. In case a match is detected between the time progression of at least one of the characteristic parameters and the predefined template, the start loop condition is detected. The template may for example be a tubular pattern defining a time course of at least one of the characteristic parameters at the transition from the person's start posture to physical exercising.

Preferably, in the person's start posture, a respective characteristic parameter remains within a predefined value range, and as soon as the person starts exercising, the characteristic parameter starts changing with a rate of change that exceeds a predefined threshold. Hence, the transition from the start posture to exercising is indicated by a specific pattern of the respective characteristic parameter. By detecting this pattern, the start of the person's physical activity can be detected.

Preferably, the start loop condition is configured for detecting a transition from the person's start posture, which corresponds to a respective characteristic parameter remaining within a predefined parameter interval, to the person's exercising activity, which corresponds to an increase or decrease of the characteristic parameter with a rate of change that exceeds a predefined threshold.

Accordingly, in a preferred embodiment, the start loop condition is detected at an image frame in which a respective characteristic parameter leaves a predetermined value range and changes with at least a minimum rate of change. As long as the person is in the start posture, the characteristic parameter remains approximately constant. In the person's start posture, the characteristic parameter is confined within the predefined value range. At the start of physical activity, the characteristic parameter leaves the predefined value range and changes at a certain rate.

Preferably, detecting the start loop condition comprises detecting when a respective characteristic parameter leaves a predetermined value range corresponding to the person's start posture.

Alternatively or additionally, detecting the start loop condition may preferably comprise detecting a change of slope of at least one of the characteristic parameters' time progression. The change of the slope indicates the onset of physical exercising.

In a preferred embodiment, the setting of the start loop condition is adjusted based on real data indicating a transition from the start posture to exercising activity. From video sequences showing a person performing an exercise, an optimum transition point may be determined for each video sequence. This data may then be used for setting the start loop condition. Furthermore, this data may be used for optimising the setting of the start loop condition.

Detection of at Least One Evaluation Point

Preferably, the method comprises a step of detecting an evaluation point in the person's movement by analysing the time progression of at least one of the characteristic parameters. An evaluation point is a point in time at which the person's posture is evaluated. Preferably, the method comprises a step of detecting at least one evaluation point for evaluating the person's movement, wherein the detection is based on the time progression of at least one of the characteristic parameters indicating the person's movement. The progression of a respective characteristic parameter is well-suited for tracking the person's motion and may for example indicate the start of exercising, the progression of the movement and the end of exercising. In particular, the time progression of the characteristic parameter can be used for detecting one or more meaningful evaluation points. Preferably, each of the evaluation points corresponds to a significant posture of the person performing the exercise or to a significant point in time or to a significant point in the time progression of the movement. At a respective evaluation point, the person's respective posture is evaluated.

Preferably, for detecting at least one evaluation point for evaluating the person's movement, at least one of the following is evaluated as a function of time: the time course of at least one of the characteristic parameters, a first derivative with respect to time of at least one of the characteristic parameters and a second derivative with respect to time of at least one of the characteristic parameters. Preferably, for detecting at least one evaluation point, at least one extremum in the time course of at least one of the characteristic parameters is detected, with the at least one extremum indicating the at least one evaluation point.

Further preferably, for detecting at least one evaluation point, a time progression of at least one of the characteristic parameters is compared with a predefined template indicating a typical time behaviour of at least one of the characteristic parameters at a respective evaluation point. In case a match is detected between the time progression of at least one of the characteristic parameters and the predefined template, the at least one evaluation point is detected. The template may for example be a tubular pattern defining a time course of at least one of the characteristic parameters at a respective evaluation point.

Preferably, detecting at least one evaluation point comprises detecting when a respective characteristic parameter enters a predetermined value range corresponding to a respective evaluation point. Preferably, the respective characteristic parameter may enter the predetermined value range with at least a minimum rate of change.

Further preferably, based on the time progression of at least one of the characteristic parameters indicating the person's movement, a plurality of evaluation points for evaluating the person's movement is detected. In the course of performing an exercise, the posture can be verified at a plurality of evaluation points. Thus, the feedback can be improved. Especially for complex exercises, but not limited to complex exercises, an improved evaluation is possible.

In a preferred embodiment, at least one of the evaluation points is a point where at least one of the characteristic parameters assumes its maximum value or its minimum value in the course of the person's movement when performing the physical exercise. In many cases, the posture at the maximum value or the minimum value of the characteristic parameter is meaningful for evaluating the physical exercise.

Evaluating the Person's Posture at at Least One Evaluation Point

In a further preferred embodiment, the method comprises a step of evaluating the person's posture in a respective image frame at each evaluation point or in at least one image frame in a respective predefined time interval around each evaluation point. In case an image frame coincides with an evaluation point, the image frame at the evaluation point is the image frame that coincides with the evaluation point. In case none of the image frames coincides with the evaluation point, the image frame at the evaluation point may either be the image frame that precedes the evaluation point or the image frame that follows the evaluation point in temporal order. The respective predefined time interval around each evaluation point is short compared to the length of the loop, it may for example be less than 15% of the length of the loop or it may for example be less than 10% of the length of the loop. Preferably, the predefined time interval is at least 30 ms, further preferably at least 50 ms, further preferably at least 100 ms, further preferably at least 150 ms, further preferably at least 200 ms. Preferably, the predefined time interval is less than 500 ms, further preferably less than 400 ms, further preferably less than 300 ms. In particular, it is determined whether the posture is a favourable posture. Preferably, evaluating the person's posture comprises evaluating the respective positions of at least a subset of the body key points indicating the person's posture in a respective image frame. For evaluating the person's posture, in addition to the respective positions of at least a subset of the body key points indicating the person's posture, further parameters like for example velocity or acceleration of at least one body key point etc. may for example be considered. From the subset of body key points, the orientation of different parts of the body can be obtained and used as a basis for evaluating the posture.

In a preferred embodiment, the person's posture in respective image frames at one of the evaluation points is compared with a preconfigured pose, for example with an ideal preconfigured pose. Preferably, a deviation between the person's posture in at least one image frame at one of the evaluation points and the preconfigured pose is detected.

Preferably, evaluating the person's posture comprises comparing the person's posture with a set of predefined conditions. These conditions specify a favourable posture at a respective evaluation point of the physical exercise. When the person's posture corresponds to this favourable posture, the exercise is performed in the right way. In contrary, if the person's posture deviates from this favourable posture, corrections are required.

In a preferred embodiment, the evaluation comprises determining whether the person's posture at a respective evaluation point is within the limits imposed by a set of predefined conditions. If each of the conditions is fulfilled, the posture is within the limits imposed by said conditions, and accordingly the exercise is performed in the right way.

Preferably, the at least one characteristic parameter used for detecting the at least one evaluation point is the same at least one characteristic parameter that is used for detecting the start loop condition. Accordingly, the same characteristic parameters can be used for detecting the start loop condition and for detecting the at least one evaluation point. In addition, the at least one characteristic parameter may for example be used for detecting an end loop condition.

In an alternatively preferred embodiment, at least one of the characteristic parameters used for detecting the evaluation point is a different parameter than the at least one characteristic parameter used for detecting the start loop condition. For example, the start loop condition may be detected based on a Procrustes distance, whereas the at least one evaluation point may be detected based on a coordinate value of a body key point.

Providing Feedback to the Person

Preferably, a person's posture in an image frame at each evaluation point or in at least one image frame in a respective predefined time interval around each evaluation point is evaluated and in response to the result of the evaluation, a feedback is provided to the person. The feedback may for example comprise a comment on the posture or improvements may be suggested.

Preferably, based on the result of comparison between the person's posture at one of the evaluation points and a set of predetermined feedback trigger conditions, feedback is provided to the person. Preferably, the method comprises a step of evaluating the person's posture in at least one image frame at the respective evaluation point by comparing the posture with a set of predefined feedback trigger conditions, the feedback trigger conditions being configured for triggering a feedback to the person. In this embodiment, the conditions for specifying a favourable posture are used for triggering a feedback to the person in case the respective condition is not met. In this respect, the feedback trigger conditions trigger the display of feedback messages to the person. Each time the respective condition is not met, a suitable feedback is provided to the person.

Further preferably, the evaluation comprises determining whether the person's posture at one of the evaluation points is within the limits imposed by a set of predefined feedback trigger conditions. Further preferably, in case the person's posture at one of the evaluation points is outside the limits imposed by at least one of the predefined feedback trigger conditions, a corresponding feedback is provided to the person. For each of the feedback trigger conditions, at least one corresponding message for providing a feedback may be provided. In case the respective feedback trigger condition is not met, a feedback message specifically suited for this condition is displayed.

Preferably, each time the person's posture is outside a limit defined by one of the predefined feedback trigger conditions, a corresponding feedback is provided to the person. The feedback may for example contain suggestions on how to improve the posture.

Preferably, the feedback provided to the person comprises at least one of audio feedback, textual feedback and graphical feedback. In an especially preferred embodiment, the feedback provided to the person comprises displaying an audio recording including comments on the person's posture. In these audio recordings, typical problems that occur when performing the exercise are addressed.

Preferably, the predefined feedback trigger conditions comprise at least one of distances, ratios, proportions and angles between body key points of the set of body key points and specific relationships between different body key points.

In a further preferred embodiment, a deviation between the person's posture at one of the evaluation points and a preconfigured pose is detected and based on the deviation, feedback is provided to the person.

In a preferred embodiment, the method comprises adjusting the setting of the feedback trigger conditions based on real data indicating optimum trigger conditions. Thus, the limits imposed by the feedback trigger conditions can be adjusted and optimised.

Detecting an End Loop Condition

Preferably, the method comprises detecting an end loop condition by evaluating the time progression of at least one of the characteristic parameters, said end loop condition indicating a transition from the person's movement when performing the physical exercise to an intermediate posture. The intermediate posture is the posture at which the respective physical exercise ends. The intermediate posture may for example be a static posture or it may for example comprise an intermediate motion, for example a regular intermediate motion. Preferably, the intermediate posture is a rest position. Based on the time progression of at least one of the characteristic parameters, both the start loop condition and the end loop condition may be determined. As a result, the start of the loop and the end of the loop are determined, with the loop corresponding to one single repetition of the physical exercise.

Preferably, the method comprises deriving the time period for a single loop of the physical exercise based on the start of the loop and the end of the loop. Preferably, the time period for a single loop of the physical exercise is determined as a time difference between a start of the loop and an end of the loop. Preferably, the time period for a single loop of the physical exercise is evaluated. Further preferably, based on the evaluation of the time period, feedback is provided to the person. Preferably, the time period for a single loop is compared with at least one of a lower threshold and an upper threshold. In case the time period is below a lower threshold, feedback is provided to the person indicating that the exercise has been performed too fast. Further preferably, in case the time period is above an upper threshold, feedback is provided to the person indicating that the exercise has been performed too slowly.

Preferably, the end loop condition defines the end of a loop encompassing one single repetition of the physical exercise.

Preferably, the start loop condition and the end loop condition define a loop encompassing one single repetition of the physical exercise. By detecting the start loop condition and the end loop condition, the loop of exercising can be determined. The loop provides an intrinsic time frame for analysing and evaluating the person's exercising activity. Accordingly, by determining the intrinsic time period of the loop, analysing the time course of the person's movements when the person is doing physical exercises is simplified.

In a preferred embodiment, a step of evaluating the person's posture is performed at at least one evaluation point during the loop delimited by the start loop condition and the end loop condition. Preferably, a time period between a start of the loop and a specific evaluation point or a time period between a specific evaluation point and an end of loop is determined. Further preferably, a time period between two selected evaluation points is determined. Preferably, based on an evaluation of any of these time periods, feedback is provided to the person. Preferably, any of these time periods is compared with at least one threshold. In dependence on the outcome of the comparison, suitable feedback may for example be provided to the person.

Preferably, the method comprises a step of adjusting the setting of the end loop condition based on real data indicating an optimum transition from exercising activity to an intermediate posture.

Preferably, the steps of the above described methods for monitoring a person performing a physical exercise are executed on a mobile device. In particular, the step of extracting, based on the sequence of image frames, for each image frame a set of body key points using a neural network is executed on a mobile device. Preferably, the mobile device is one of a smartphone, a tablet, a laptop.

Preferably, the sequence of image frames is acquired using a camera. Preferably, the sequence of image frames is acquired using a 2D camera or a 2.5D camera or a 3D camera. The method can be performed using a common 2D camera, which is available in most smartphones. Alternatively, the method may also be performed using a 2.5D camera or a 3D camera. Preferably, the sequence of image frames acquired by the camera comprises additional depth information. The additional depth information may be used for improving the results of the evaluation. Further preferably, the sequence of image data is acquired using a camera of a mobile device. Preferably, the mobile device is one of a smartphone, a tablet, a laptop.

Preferably, for each image frame of the sequence of image frames, the body key points are extracted using a convolutional neural network, wherein the convolutional neural network is configured for extracting, for each image frame showing the person, a set of body key points indicating the person's posture. Convolutional neural networks are well-suited for performing image analysis. A convolutional neural network with a stacked hourglass architecture is described in the article by A Newell, K Yang and J Deng "Stacked hourglass networks for human pose estimation", European Conference on Computer Vision, October 2016, pp 483-499, Springer International Publishing, https://arxiv.org/abs/1603.06937. For adapting the convolutional neural network to the limitations imposed by the processing resources on a smartphone, reference is made to the article by A G Howard, M Zhu, B Chen, D Kalenichenko, W Wang, T Weyand, M Andreetto and H Adam, "Mobilenets: Efficient convolutional neural networks for mobile vision applications", 2017, arXiv preprint arXiv:1704.04861, https://arxiv.org/abs/1704.04861. In a preferred embodiment, a Sequence Model such as a Recurrent Neural Network could be used to extract the body key points from a plurality of image frames. Here, the image frames are provided as input to the Neural Network one after another in temporal order as taken from the camera stream. The Neural Network preserves an internal state and thus incorporates information from image frames that were processed in the past in order to compute more accurate body key points for the one image frame that was provided as the last input. More information related to the use of sequence models for computing body key points can be found in the article by M R Hossain and J J Little, "Exploiting temporal information for 3D pose estimation", 2017, CoRR, https://arxiv.org/abs/1711.08585. Preferably, the neural network is configured for extracting, for each image frame, 2D body key points. In an alternatively preferred embodiment, the neural network is configured for extracting, for each image frame, 2.5D or 3D body key points.

BRIEF DESCRIPTION OF THE DRAWING

The invention is illustrated in greater detail with the aid of schematic drawings. It shows schematically:

FIG. 3a shows a subset of the body key points related to the hip, the knee and the ankle when the person stands straight.

FIG. 3b shows the subset of body key points of FIG. 3a when the person does a squat.

FIG. 4a depicts the Procrustes distance relative to a person's start posture as a function of time during exercising.

FIG. 4b depicts the Procrustes distance relative to a person's posture at an evaluation point as a function of time during exercising.

DETAILED DESCRIPTION OF EMBODIMENTS OF THE INVENTION

Figure 1:
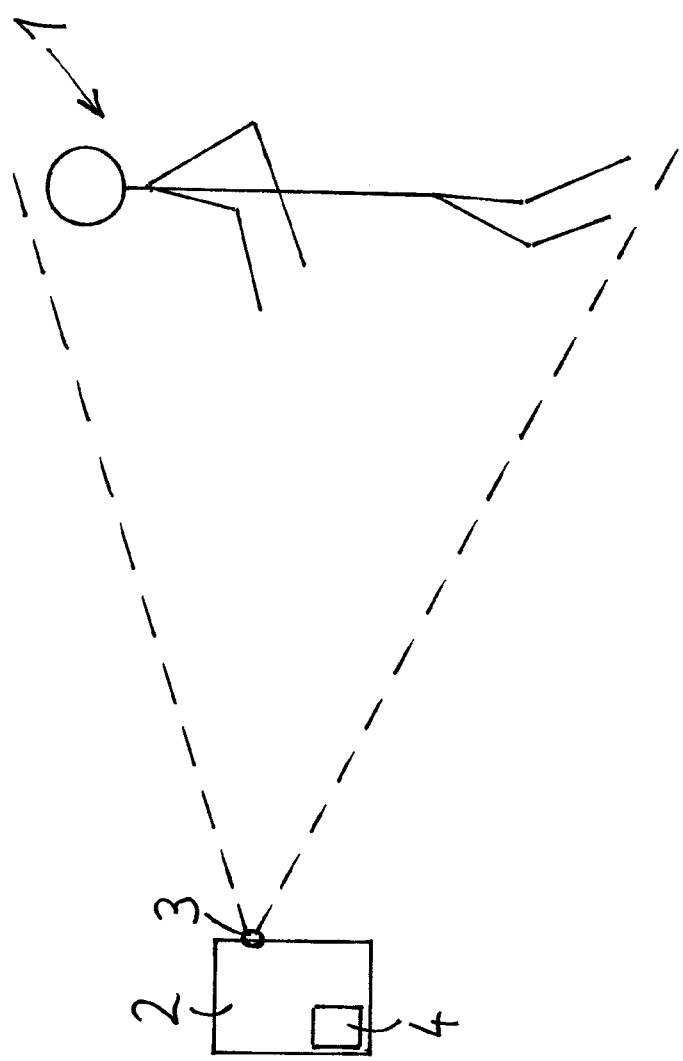
FIG. 1 shows a mobile device with a camera configured for acquiring a sequence of image frames of a person performing physical exercises.

In the following description of preferred embodiments of the present invention, identical reference numerals denote identical or comparable components.

FIG. 1 shows a person 1 performing a physical exercise, for example a squat. To make sure that exercising is performed correctly, a mobile device 2 with a camera 3 is placed at a distance from the person. Preferably, the mobile device 2 is arranged such that the entire body of the person 1 is within the camera's field of view. In this position, the mobile device 2 can acquire a sequence of image frames, preferably a video sequence, of the person's movement. The mobile device 2 may for example be a smartphone, a tablet, a laptop, etc. An evaluation unit 4 configured for analysing the person's movements and for providing feedback to the person may for example be installed on the mobile device 2. Thus, the processing of the sequence of image frames is performed on the mobile device 2. Alternatively, instead of using a mobile device, a stationary computer with a camera may be used for image data acquisition and data processing.

Further alternatively, a mobile device may comprise a camera for acquiring a sequence of image frames and an interface for transmitting the image data to a remote computer or to a cloud server. Preferably, the interface is an interface for wireless data transmission. Processing of the sequence of image frames and the extraction of body key points may be performed on the remote computer or on the cloud server, and at least some of the results of these computations and/or feedback for the user may be transmitted from the remote computer or cloud server back to the mobile device.

According to yet another alternative example, a camera may be connected to a transmitter configured for transmitting a sequence of image data to a remote computer or to a cloud server. In this case, processing of the sequence of image frames is performed on the remote computer or on the cloud server. Optionally, feedback for the user may be transmitted from the remote computer or the cloud server back to the transmitter and the transmitter may be configured for providing feedback to the person performing a physical exercise.

The evaluation unit 4 is configured for extracting, for each of the acquired image frames, respective positions of a predefined set of body key points. The body key points may for example be assigned to the joints of the body and to body features like for example the forehead, the chin, the breastbone, the hip, etc. The extraction of the body key points is performed using a neural network, preferably a convolutional neural network (CNN). The image data of an image frame is fed to the input layer of the convolutional neural network, which processes the image data in several consecutive processing layers. The convolutional neural network has been trained to recognise the respective position of body key points in the image data. For each predefined body key point, an associated two-dimensional output matrix is generated, with the respective position of the body key point being indicated in the two-dimensional output matrix. Preferably, the two-dimensional output matrix indicates respective probabilities for each point that the body key point is located at that point. The point having the highest probability is taken as the body key point's position. For each of the predefined body key points, the convolutional neural network provides a separate output matrix indicating the position of one specific body key point. In addition to the position of the body key point, the probability associated with the body key point's position may be considered during further computation. For example, if a particular joint or limb is not visible, the associated probability will be comparatively low. In this regard, the probability indicates a level of confidence of the obtained results.

In a preferred embodiment, a Sequence Model such as a Recurrent Neural Network or a Long-Short-Term-Memory might take in a sequence of image frames, wherein for each new image frame, the body key points for the new image frame are output based on latent temporal information of at least one of the past image frames. More information related to latent temporal information in neural networks can be found in the article by M R Hossain and J J Little, "Exploiting temporal information for 3D pose estimation", 2017, CoRR, https://arxiv.org/abs/1711.08585. As far as latent temporal information in neural networks is concerned, this article is herewith incorporated by reference.

The neural network may be configured for extracting body key points in 2D from the sequence of image frames. Alternatively, 3D body key points may be derived for a 2D (or 2.5D) image frame or for a sequence of 2D (or 2.5D) image frames, wherein the 2D or 2.5D image frames are acquired using a 2D or 2.5D camera. Using the techniques of machine learning, it is possible to derive additional depth information even for a 2D image frame.

Mainly because of body constraints, it is possible to estimate the additional depth information for each body key point. For determining the additional depth information, the neural network may for example comprise an additional depth regression module. Further alternatively, the neural network may be configured for extracting body key points in 3D from the sequence of 3D image frames.

For implementing a convolutional neural network (CNN) capable of extracting body key points from the sequence of image frames, a stacked hourglass architecture as described in the article by A Newell, K Yang and J Deng "Stacked hourglass networks for human pose estimation", European Conference on Computer Vision, October 2016, pp 483-499, Springer International Publishing, https://arxiv.org/abs/1603.06937 is used. The input layer is a 256×256×3 layer comprising 256×256 pixels and 3 colour channels per pixel, for example RGB colour channels. In the present implementation, the convolutional neural network comprises four hourglass modules. As an output of the convolutional neural network, 16 matrices corresponding to the 16 body key points are obtained, with each matrix comprising 64×64 pixels. Each point of the matrix indicates a probability that the respective body key point is located at that point. Regarding the implementation and structure of the hourglass modules, the above referenced article "Stacked hourglass networks for human pose estimation" is herewith incorporated by reference. The stacked hourglass architecture has been adapted to the limitations imposed by the limited processing resources on a smartphone. In this respect, reference is made to the article by A G Howard, M Zhu, B Chen, D Kalenichenko, W Wang, T Weyand, M Andreetto and H Adam, "Mobilenets: Efficient convolutional neural networks for mobile vision applications", 2017, arXiv preprint arXiv:1704.04861, https://arxiv.org/abs/1704.04861. With regard to implementation of a convolutional neural network with a stacked hourglass architecture on a smartphone, this article is herewith incorporated by reference. Based on the 2D hourglass approach, for example a depth regression module may be added after a stack of hourglass modules to output a vector of size 16 (for 16 key points) which encodes the depth information in addition to the 64×64×16 shaped matrices that have been described so far. Details of the depth regression module can be found in the article by X Zhou, Q Huang, X Sun, X Xue and Y Wei, "Towards 3d human pose estimation in the wild: a weakly-supervised approach", October 2017, IEEE International Conference on Computer Vision, https://arxiv.org/abs/1704.02447. A further approach to determining depth information is presented in the article by J Martinez, R Hossain, J Romero and J J Little, "A simple yet effective baseline for 3d human pose estimation", May 2017, IEEE International Conference on Computer Vision, Vol. 206, p. 3, https://arxiv.org/abs/1705.03098. As far as the addition of depth information is concerned, these two articles are herewith incorporated by reference.

Figure 2:
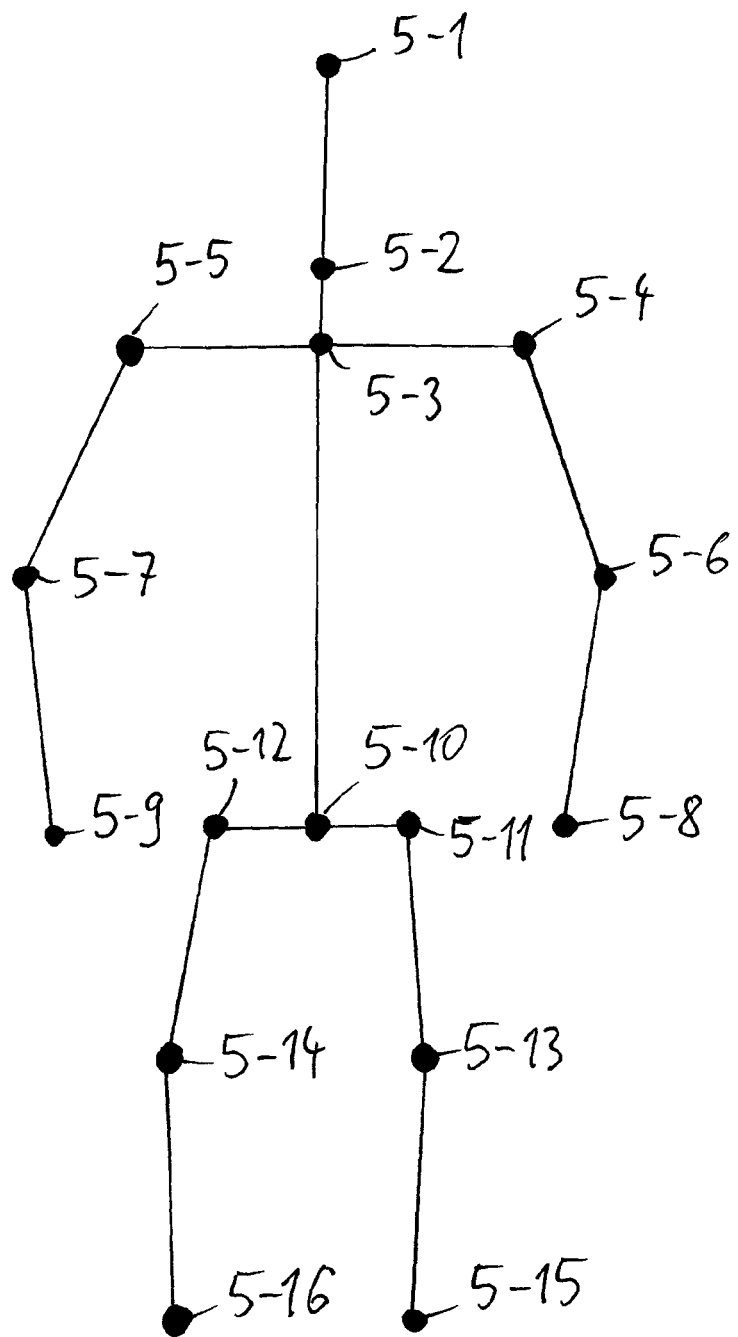
FIG. 2 shows a set of body key points indicating the person's posture.

FIG. 2 shows an example of a posture of a person's body, wherein the posture is described by the respective positions of sixteen different body key points 5-1 to 5-16. The body key points form a skeleton of the human body and allow for detecting the orientation of different parts of the body relative to each other. The body key points 5-1 to 5-16 may be 2D body key points, but they may as well be 2.5D or 3D body key points. By tracking the positions of the body key points in the acquired sequence of image frames, the person's movements when performing a physical exercise can be evaluated.

Initially, before exercising is started, the person is asked by the mobile device 2 to assume a predefined setup position. In the setup position, the person stands straight, with the distance between the feet being shoulderwide. The evaluation unit 4 extracts the respective positions of the body key points 5-1 to 5-16. In addition, the evaluation unit 4 detects if the person's posture corresponds to the predefined setup position. For this purpose, the evaluation unit 4 analyses at least one of ratios, proportions, positions, distances and angles of the obtained posture, in order to detect whether the person is in the setup position. For example, the upright stand of the person in the setup position may be identified by relating the distance between the two shoulders to the distance between thorax and pelvis. Based on the evaluation of predefined geometric properties, the evaluation unit 4 recognises that a front view of a person in the setup position is captured. The respective positions of the body key points in the person's setup position may then for example be used for calibrating the dimensions and proportions of the person's body.

Optionally, the person may be asked by the mobile device 2 to turn sideways by 90°, such that a side view of the person can be acquired as a second setup position. In the second setup position, acquiring a side view of the person may yield additional information on the properties and proportions of the person's body.

After the person's posture in the respective setup positions has been detected and acquired, the person is asked by the evaluation unit 4 to start performing a specific physical exercise like for example a squat. The person may either perform a single pass of the physical exercise or a number of repetitions of the physical exercise. In the following, a single pass of the physical exercise will be referred to as a "loop" of physical exercising. In the present case, the person is in the second setup position oriented sideways to the camera when exercising starts. Accordingly, the second setup position will be the start posture for exercising. The start posture is the posture from which the respective physical exercise is started. When performing the physical exercise, the person starts at a start posture, performs the physical exercise and comes to an intermediate posture. Then, further repetitions may be performed.

Determining a Characteristic Parameter for Tracking Exercising Activities

In order to track and evaluate the person's exercising activity, at least one characteristic parameter indicating a time progression of the person's movement is derived from the respective positions of a subset of the body key points in the image frames of the sequence of image frames. By analysing the time progression of a respective characteristic parameter in the course of exercising, it is possible to detect a start of the loop, wherein the start loop condition indicates the transition from the person's start posture to the person's movement when performing the exercise. Furthermore, the time progression of the characteristic parameter allows detecting an end loop condition, with the end loop condition denoting a transition between the person's movement during exercising and an intermediate posture after the first repetition of the exercise has been performed. In the following, different ways of determining a characteristic parameter for tracking the motion will be explained.

A first option is to use a coordinate value of a specific body key point as a characteristic parameter for tracking the person's movements. For example, the vertical coordinate value of the person's hip may be taken as a characteristic parameter for tracking the execution of squats. Alternatively, a characteristic parameter may be derived from coordinate values of a plurality of different body key points. For example, the coordinate values of a subset of the body key points may be taken as a basis for calculating the characteristic parameter. For example, the characteristic parameter may be derived by determining an average value of several different body key points. In addition to the coordinate values, probabilities for each body key point obtained as an output of the neural network may be taken into account, for example as a sanity criterion.

A second option for determining a characteristic parameter indicative of the person's movement is based on the evaluation of the Procrustes distance. The Procrustes distance of a subset of body key points relative to the same subset of body key points in a reference frame, for example in an image frame showing the person's start posture, is used as a characteristic parameter indicating the course of the person's movement when performing the physical exercise.

In a first step, a subset of body key points is selected in dependence on the respective physical exercise to be monitored. For example, when performing a squat, the seven body key points related to the lower back, the left and right hip, the left and right knee and the left and right ankle may be used as a suitable subset of body key points. FIG. 3a shows the respective positions of these body key points 6-1 to 6-7 for the person in its start posture, whereas FIG. 3b shows the same subset of body key points 6-1 to 6-7 when the person has lowered the body and bent the knees. As a characteristic parameter, the Procrustes distance between these two configurations of body key points is determined. In a Procrustes analysis, the two subsets of body key points are brought into alignment as far as possible by performing steps of scaling, translating, rotating and reflecting, in order to eliminate any difference in size and orientation of the two configurations of body key points. After these simple transformations have been performed, there still exists a difference in shape between the two configurations of points. The Procrustes distance is obtained as the L2 norm of the remaining differences between the two subsets after the transformation. In particular, the Procrustes distance is obtained by summing up the squared differences between the coordinate values of the points in the first subset and the second subset. The Procrustes distance provides a measure of the difference in shape between the two configurations of points. For this reason, the Procrustes distance is well-suited for tracking the motion of the person when performing the exercise.

If X denotes the positions of the subset of body key points in the person's start posture, which is used as a reference, and Y denotes the positions of the body key points at an arbitrary evaluation point in the course of exercising, X and Y can be brought into an alignment by scaling, rotating, translating and reflecting the two subsets X and Y relative to one another. For performing these transformations, the following expression is minimised:

$$\|Y-(1c^T+\rho XA)\|$$

where X and Y are the input matrices, 1 is the unit matrix, c is a row vector representing the translation, $\rho$ is the scalar "dilation factor", A is the rotation and reflection matrix (orthogonal, oblique or unrestricted) and $\|.\|$ denotes the L2 norm. By minimising the above expression, the row vector c for the translation, the scalar dilation factor $\rho$ and the rotation and reflection matrix A are obtained. Furthermore, by performing the minimising process, the Procrustes distance between the subsets X and Y is obtained, because the minimised expression $\|Y-(1\ c^T+\rho XA)\|$ is the Procrustes distance between the two subsets X and Y. The Procrustes distance can be determined in 2D between two configurations of 2D body key points, but it can also be determined in 2.5D or 3D between two configurations of 2.5D or 3D body key points. Accordingly, a characteristic parameter based on the Procrustes distance may be used based on 2D body key points for indicating a progression of the person's movement, but it can also be used based on 2.5D or 3D body key points for indicating a progression of the person's movement.

A third option is to apply a filtering operation to a subset of the body key points in the sequence of image frames and to obtain, as a result of the filtering operation, at least one of the characteristic parameters. For example, a Kalman filter may be applied to a subset of body key points for determining at least one of the characteristic parameters. Kalman filtering is an algorithm that uses a series of measurements observed over time, containing statistical noise and other inaccuracies, and produces estimates of unknown variables that tend to be more accurate than those based on a single measurement alone, by estimating a joint probability distribution over the variables for each timeframe. The Kalman filter is an efficient recursive filter that estimates the internal state of a linear dynamic system for a series of noisy measurements. The algorithm works in a two-step process. In the prediction step, the Kalman filter produces estimates of the current state variables, along with their uncertainties. Once the outcome of the next measurement is observed, which is necessarily corrupted with some amount of error, including random noise, these estimates are updated using a weighted average, with more weight being given to estimates with higher certainty. By subjecting a subset of body key points in the sequence of image frames to Kalman filtering, estimates of at least one of velocity and acceleration of at least one of the body key points are determined as characteristic parameters indicating a progression of the person's movement. For example, linear velocity or angular velocity of a respective body key point or an angle enclosed by specific body key points may be obtained as a result of Kalman filtering.

As a fourth option, at least one of the characteristic parameters is derived from a subset of body key points in the sequence of image frames using machine learning. For example, at least one characteristic parameter may be derived that it is suitable for detecting a transition from the person's start posture to exercising. As a further example, at least one characteristic parameter may be derived that it is suitable for detecting at least one evaluation point in the course of the person's movement. For example, at least one of the characteristic parameters may be learned using a statistic model. The model could for example map a subset of body key points to the interval [0, 1] as a probability to indicate the start of the loop or as a probability to indicate a respective evaluation point.

Detecting a Start Loop Condition

For evaluating the person's movement when performing the physical exercise, it is essential to detect the transition from the start posture to exercising activity. The detection of this transition is performed based on the time progression of at least one of the characteristic parameters. For detecting this transition, a start loop condition is used, wherein this start loop condition is configured such that the transition from the start posture to physical exercising can be detected. The start loop condition is applied to the time progression of at least one of the characteristic parameters. If it is detected that the start loop condition is fulfilled for a certain image frame, this means that the person's exercising activity starts at this image frame.

In FIG. 4a, a characteristic parameter indicating the person's motion is shown as a function of time. The time axis also corresponds to the sequence of image frames, because in general, the image frames of for example a video sequence are acquired at regular time intervals. The characteristic parameter shown in FIG. 4a is the first Procrustes distance, the first Procrustes distance being the Procrustes distance of a subset of body key points relative to the same subset of body key points in an image frame showing the start posture. Hence, for determining the first Procrustes distance, the image frame showing the person's start posture is taken as a reference frame.

In FIG. 4a, curve 7 shows the first Procrustes distance as a function of time during a single pass of exercising. For each image frame, the first Procrustes distance, which is the Procrustes distance of a subset of body key points relative to the same subset of body key points in an image frame showing the start posture, is calculated.

During a time interval 8, the person is in a start posture. Therefore, during the time interval 8, the first Procrustes distance remains approximately constant. Then, at the point of time 9, the person starts performing a physical exercise like for example a squat. When the person starts bending the knees and lowering the body, the first Procrustes distance increases, because the first Procrustes distance indicates the change of the person's posture relative to the start posture. During the time interval 10, the person performs the physical exercise. At the time point 11, the physical exercise is finished and the person is in an intermediate posture, for example in a rest position. Therefore, during the time interval 12, the first Procrustes distance remains approximately constant.

The point of time 9, which indicates the start of the physical exercise, is detected by means of a start loop condition. The start loop condition is configured for detecting the transition from the person's start posture to exercising activity based on the time progression of the characteristic parameter. When the person is in the start posture, it is detected for each image frame whether or not the start loop condition is fulfilled. Detecting the start loop criterion may for example comprise detecting the characteristic change in slope of the curve 7 at the point of time 9. In particular, a change of the slope from a nearly horizontal slope to a slope 13 that exceeds a predefined threshold may be detected. Furthermore, the characteristic parameter remains nearly constant during the time interval 8, with the characteristic parameter being confined to a value range 14. Hence, detecting the start loop condition may comprise determining when the characteristic parameter leaves the predefined value range 14. In this regard, when the characteristic parameter leaves the value range 14, this indicates the start of the person's exercising activity.

In a preferred example, the evaluation unit 4 detects in a first step if the characteristic parameter is within the predefined value range 14. As soon as the characteristic parameter leaves the predefined value range 14, the evaluation unit 4 determines if the rate of change exceeds a predefined threshold. If this is the case, it is detected that the start loop condition is fulfilled for the image frame at the point of time 9. Hence, the start of loop is detected. The start loop condition may alternatively be defined by specifying a transition template describing a transition from the person's start posture to exercising activity. For example, the template may model the typical time behaviour of the characteristic parameter at the transition from the start posture to exercising activity at the start of loop. When a match between the time progression of the characteristic parameter and the time behaviour described by the predefined template is detected, the start of loop is detected.

The definition of the start loop condition is essential for monitoring the person's physical activity, because it allows detecting a time frame related to a start of the loop of exercising, said loop corresponding to one single pass of the physical exercise.

Preferably, the start loop condition is adjusted and optimised in dependence on real video sequences of persons performing the exercises. For example, for a large number of video sequences, the optimum transition point may be specified manually, and this large amount of reference data may be used for optimising the start loop condition. For example, machine learning using a neural network may be used for adjusting the start loop condition. In this way, the start loop condition can be adapted to real data showing persons performing the exercise.

Evaluating the Person's Posture at at Least One Evaluation Point

When the person performs the physical exercise, the person's posture is evaluated at one or more predefined evaluation points in the course of exercising. These evaluation points are detected by evaluating a time progression of at least one characteristic parameter indicating the person's movement. At the one or more evaluation points, the person's posture is evaluated. One or more of the at least one characteristic parameters used for detecting the at least one evaluation point may be identical to the at least one characteristic parameter used for detecting the start loop condition. In particular, the at least one evaluation point may for example be detected in dependence on the same characteristic parameters that are used for detecting the start loop condition.

Returning to the above example of a person doing squats, a relevant evaluation point is the point where the person's body reaches the lowest position and the person's knees are bent. In this position, the person's hands are approximately on the same level as the knees. In the diagram shown in FIG. 4a, this evaluation point 15 corresponds to the maximum value of the first Procrustes distance. Accordingly, for detecting the evaluation point 15, the point where the first Procrustes distance reaches its maximum is determined. For example, it is determined where the first derivative with respect to time of the curve 7 is equal to zero.

At the evaluation point 15, the person's posture is evaluated. Evaluating the person's posture comprises evaluating respective positions of a subset of the body key points in a respective image frame. Depending on the result of this evaluation, suitable feedback is provided to the person performing the exercise. For example, typical errors and shortcomings when performing the exercise may be detected. In dependence on the respective deficiencies, a prerecorded audio message with comments on the person's posture may be reproduced.

The progression of the person's movement may additionally be monitored by tracking a second characteristic parameter, wherein analysis of the second characteristic parameter complements analysis of the first characteristic parameter. In FIG. 4b, the time progression of the second characteristic parameter is shown as a function of time. The second characteristic parameter is a second Procrustes distance, the second Procrustes distance being the Procrustes distance of the subset of body key points in an image frame relative to the subset of body key points in a reference frame at the evaluation point 15 where the person's body has reached the lowest position and the person's knees are bent. While the first Procrustes distance shown in FIG. 4a is determined relative to the subset of body key points in the start posture, the second Procrustes distance shown in FIG. 4b is determined relative to a subset of body key points at the evaluation point 15.

In FIG. 4b, the curve 16 indicates the time progression of the second Procrustes distance as a function of time. During the time interval 8, the second Procrustes distance is comparatively large, because in the start posture, the person's posture differs considerably from the posture at the evaluation point 15. At the point of time 9, the person starts performing a squat. When the person bends the knees, the second Procrustes distance becomes smaller and smaller and at the evaluation point 15, the second Procrustes distance reaches its minimum, because the person's posture coincides with the posture in the reference frame at the evaluation point 15. When the second Procrustes distance reaches its minimum and enters a predefined value range 17, it is detected that the evaluation point 15 is reached. The person's posture at the evaluation point 15 is analysed. When the person returns to its upright position, the second Procrustes distance increases. At the point of time 11, the exercise is finished and the person has returned to the upright position. Accordingly, during the time interval 12, the second Procrustes distance is as large as at the beginning.

Figure 5:
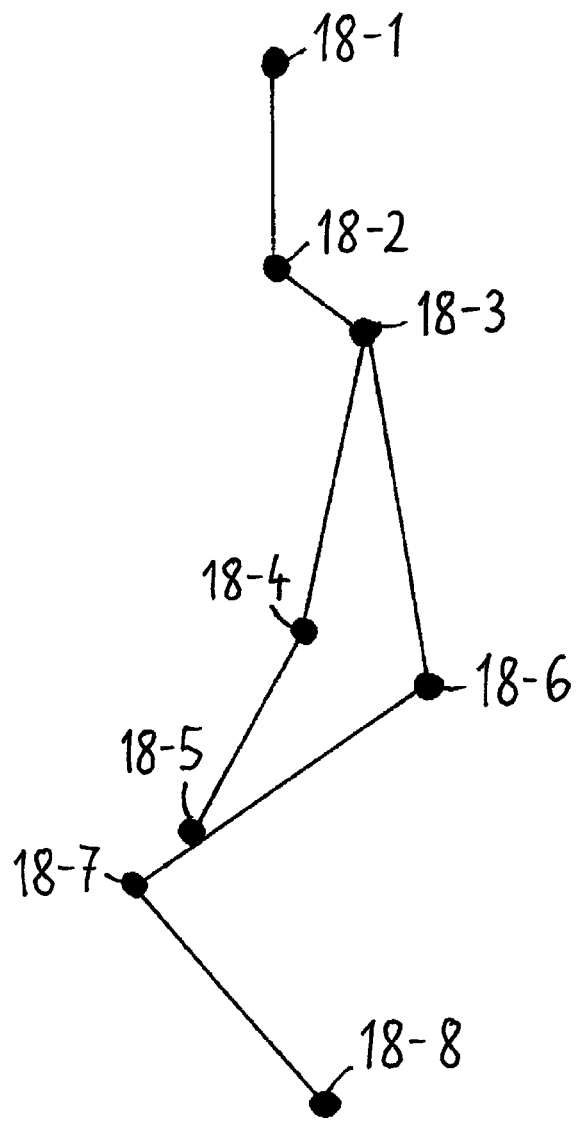
FIG. 5 gives a side view of the person's posture when the person has reached the lowest position.

FIG. 5 shows the person's posture at the evaluation point 15. For evaluating the posture as indicated by the subset of body key points 18-1 to 18-8, a set of predefined conditions is defined. If the posture represented by the body key point 18-1 to 18-8 meets each of these conditions, the posture is in conformity with the requirements. In case one or more of the predefined conditions are not met, a prerecorded audio message that corresponds to this error is selected and displayed to the person. Accordingly, the set of predefined conditions can be referred to as a set of feedback trigger conditions. In case the posture is indicated by a set of 2D body key points, the feedback trigger conditions may define conditions for evaluating the posture in two dimensions. In case the posture is indicated by a set of 3D body key points, the feedback trigger conditions may be set up in a three dimensions. Alternatively, a posture defined by the set of 3D body key points may be projected to one or more two-dimensional projection planes. Thus, a dimensional reduction is accomplished. Then, the person's posture can be evaluated in the two-dimensional projection plane by applying a set of feedback trigger conditions in two dimensions. The advantage is that the orientation of the two-dimensional projection plane can be chosen in dependence on the orientation of the person's posture. Further preferably, the posture defined by the set of 3D body key points may be projected on a plurality of two-dimensional projection planes. For one specific frame, the pose may for example be evaluated from multiple perspectives based on multiple 2D constraints applied to the different projections.

For evaluating the posture shown in FIG. 5, a plurality of different feedback trigger conditions may be defined. The feedback trigger conditions may for example specify at least one of distances, angles, ratios of different body parts and specific relationships between different body key points. For each feedback trigger condition, an allowable deviation from the given condition may for example be specified. The feedback trigger conditions may for example be set up using an editor or a graphical user interface provided for this purpose. For example, a physiotherapist may use such a tool for specifying the feedback trigger conditions for dedicated postures of a certain physical exercise.

For example, for the above example of a squat, a first feedback trigger condition may define that the head is oriented at an angle of 0° relative to the vertical, in order to make sure that the line of sight is straight. For this condition, an allowable deviation of 5° may be specified. A second feedback trigger condition may specify that the leg is oriented at angle of less than 45° relative to the vertical. This ensures that the knee does not dodge to the front. The third feedback trigger condition relates to the vertical position of the wrist relative to the knee. The movement should not be too deep and therefore, the wrist has to be located above the knee. In a fourth feedback trigger condition, the correct orientation of the spine is defined. When doing a squat, the spine must not be crooked. Accordingly, the angle of the spine relative to the vertical should be below 40°, with an allowable deviation being set to 5°.

In case one of the feedback trigger conditions is not fulfilled, for example in case the person's wrist is located below the knee, a corresponding audio message may be reproduced. In this example, the audio message would suggest that the movement should not be that deep. The feedback provided to the person can also depend on the previously given feedback. For example, if the user has improved since the last loop but the movement is still not correct, there might be a different feedback like for example "better, but still a bit too deep". In case the person overcorrected the movement based on the last feedback, a suitable audio message may address this overcorrection.

Also with regard to the feedback trigger conditions, the limit values of these conditions may be adjusted in dependence on real data showing persons performing an exercise. For example, a physiotherapist or a physician may classify postures in a large number of video sequences, with the postures being rated as favourable or as not favourable. Depending on these ratings, the limit values and thresholds of the feedback trigger conditions may be set or adjusted automatically. Also here, suitable limit values may be either obtained as a result of calculation or by machine learning.

Detection of the End Loop Condition

At the end of the loop, there is a transition from the person's exercising activity to an intermediate posture. This transition occurs at the point of time 11. As shown in FIG. 4a, detecting the end loop condition may comprise detecting a change in the slope 19 of the curve 7 and/or detecting that the characteristic parameter remains within a value range 20 when the person is in the intermediate posture. Preferably, the intermediate posture is a rest position.

By detecting the start loop condition and the end loop condition, the loop of exercising can be detected. The loop provides a reference frame for analysing and evaluating the person's movement. Preferably, the time period for a single loop may be evaluated and compared with at least one of a lower limit and an upper limit. If the time period for performing a single repetition of the physical exercise is too short, a suitable feedback may be provided to the person performing the exercise. For example, the person may be asked to slow down when performing the exercise. If the time period for a single loop is too large, the person may be asked to perform the exercise faster.

The features described in the above description, claims and figures can be relevant to the invention in any combination. Their reference numerals in the claims have merely been introduced to facilitate reading of the claims. They are by no means meant to be limiting.

LIST OF REFERENCE NUMERALS

1 person
2 mobile device
3 camera
4 evaluation unit
5-1 to 5-16 body key points
6-1 to 6-7 subset of body key points
7 curve
8 time interval
9 point of time
10 time interval
11 point of time
12 time interval
13 slope
14 value range
15 evaluation point
16 curve 17 value range
18-1 to 18-8 subset of body key points
19 slope
20 value range

The invention claimed is:
1. A method for monitoring a person performing a physical exercise based on a sequence of image frames showing an exercise activity of the person, the method comprising:
extracting, via a smartphone or tablet, based on the sequence of image frames, for each image frame a set of body key points using a convolutional neural network, the set of body key points being indicative of a posture of the person in the image frame,
wherein the smartphone or tablet is positioned a distance from the person,
wherein the convolutional neural network is trained to recognize the body key points in the image frames;
deriving, based on a subset of the body key points in each image frame, at least one characteristic parameter indicating a progression of a movement of the person, wherein the at least one characteristic parameter is not equal to any coordinate value of the body key points;
automatically detecting a start loop condition by evaluating only a time progression of the at least one characteristic parameter, said start loop condition indicating a transition from a start posture of the person to the movement of the person when performing the physical exercise;
after detecting the start loop condition, analysing the time progression of at least one of the characteristic parameters to evaluate the person's movement and provide feedback to the person; and
automatically detecting an end loop condition by evaluating only the time progression of the at least one of the characteristic parameters, said end loop condition indicating a transition from the person's movement when performing the physical exercise to an intermediate posture.

2. The method according to claim 1, wherein at least one of the characteristic parameters for a respective image frame is derived from coordinate values of the body key points of the respective image frame.

3. The method according to claim 1, wherein for each of the image frames, at least one of the characteristic parameters is the Procrustes distance between the subset of body key points in a respective frame and the same subset of body key points in a reference frame.

4. The method according to claim 1, further comprising detecting the start posture of the person by comparing the person's posture in at least one image frame of the sequence of image frames with at least one predefined criterion.

5. The method according to claim 1, wherein an image frame in the start loop condition is detected defines the start of the person's exercising activity.

6. The method according to claim 1, wherein the start loop condition is detected at an image frame in which at least one of the characteristic parameters leaves a predetermined value range and changes with at least a minimum rate of change.

7. The method according to claim 1, wherein detecting the start loop condition comprises detecting when at least one of the characteristic parameters leaves a predetermined value range corresponding to the person's start posture.

8. The method according to claim 1, further comprising detecting at least one evaluation point in the person's movement by evaluating the time progression of at least one characteristic parameter indicating the person's movement.

9. The method according to claim 8, further comprising evaluating the person's posture at the at least one evaluation point.

10. A method for monitoring a person performing a physical exercise based on a sequence of image frames showing an exercise activity of the person, the method comprising:
extracting, via a smartphone or tablet,
based on the sequence of image frames, for each image frame a set of body key points using a convolutional neural network, the set of body key points being indicative of a posture of the person in the image frame,
wherein the smartphone or tablet is positioned a distance from the person,
wherein the convolutional neural network is trained to recognize body key points in the image frames;
deriving, based on a subset of the body key points in each image frame, at least one characteristic parameter indicating a progression of a movement of the person, wherein the at least one characteristic parameter is not equal to any coordinate value of the body key points;
automatically detecting a start loop condition by evaluating only a time progression of at least one of the characteristic parameters, said start loop condition indicating a transition from a start posture of the person to the movement of the person when performing the physical exercise;
detecting at least one evaluation point in the movement of the person by evaluating a time progression of the at least one characteristic parameter;
evaluating a posture of the person in a respective image frame at each evaluation point or in at least one image frame in a respective predefined time interval around each evaluation point; and
automatically detecting an end loop condition by evaluating only the time progression of the at least one of the characteristic parameters, said end loop condition indicating a transition from the person's movement when performing the physical exercise to an intermediate posture.

11. The method according to claim 10, wherein evaluating the posture of the person comprises comparing the person's posture with a set of predefined conditions.

12. The method according to claim 10, wherein, based on the result of comparison between the posture of the person and a set of predetermined feedback trigger conditions, feedback is provided to the person.

13. A smartphone or table comprising:
a camera configured to capture a sequence of image frames showing an exercise activity of a person using the smartphone or tablet; and
a controller configured to:
extract a set of body key points using a convolutional neural network for each image frame among the sequence of image frames, the set of body key points being indicative of a posture of the person in each image frame,
wherein the convolutional neural network is trained to recognize body key points in the image frames,
derive, based on a subset of the body key points in each image frame, at least one characteristic parameter indicating a progression of a movement of the person,
automatically detect a start loop condition by only evaluating a time progression of the at least one characteristic parameter, said start loop condition indicating a transition from a start posture of the person to the movement of the person when performing the physical exercise, analyse the time progression of at least one of the characteristic parameters to evaluate the person's movement and provide feedback to the person, and automatically detect an end loop condition by evaluating only the time progression of the at least one of the characteristic parameters, said end loop condition indicating a transition from the person's movement when performing the physical exercise to an intermediate posture.

14. A non-transitory computer storage readable medium comprising computer executable program code configured to perform the method according to claim 1.

15. The method of claim 1, wherein the smartphone or tablet is a smartphone.

16. The method of claim 10, wherein the smartphone or tablet is a smartphone.

17. The smartphone or tablet of claim 13, wherein the smartphone or tablet is a smartphone.

18. A smartphone or tablet comprising:
a camera configured to capture a sequence of image frames showing an exercise activity of a person using the smartphone or tablet; and
a controller configured to:
extract a set of body key points using a convolutional neural network for each image frame among the sequence of image frames, the set of body key points being indicative of a posture of the person in each image frame, wherein the convolutional neural network is trained to recognize body key points in an image frame, derive, based on a subset of the body key points in each image frame, at least one characteristic parameter indicating a progression of a movement of the person, wherein the at least one characteristic parameter is not equal to any coordinate value of the body key points, automatically detect a start loop condition by evaluating only a time progression of the at least one the characteristic parameter, said start loop condition indicating a transition from a start posture of the person to the movement of the person when performing the physical exercise, detect at least one evaluation point in the movement of the person by evaluating a time progression of the at least one characteristic parameter, evaluate a posture of the person in a respective image frame at each evaluation point or in at least one image frame in a respective predefined time interval around each evaluation point, and automatically detect an end loop condition by evaluating only the time progression of the at least one the characteristic parameters, said end loop condition indicating a transition from the person's movement when performing the physical exercise to an intermediate posture.

* * * * *

UNITED STATES PATENT AND TRADEMARK OFFICE
CERTIFICATE OF CORRECTION

PATENT NO. : 11,282,298 B2
APPLICATION NO. : 16/113507
DATED : March 22, 2022
INVENTOR(S) : Konstantin Mehl et al.

It is certified that error appears in the above-identified patent and that said Letters Patent is hereby corrected as shown below:

On the Title Page

Item (73), Assignee, Change:
"KAIA HEALTH SOFTWARE GMBH,
New York, NY (US)"
To:
--KAIA HEALTH SOFTWARE GMBH,
Munich (DE)--

Signed and Sealed this
Twentieth Day of December, 2022

Katherine Kelly Vidal
*Director of the United States Patent and Trademark Office*